United States Patent
Kaufman et al.

(10) Patent No.: US 10,640,570 B2
(45) Date of Patent: May 5, 2020

(54) CHIMERIC ANTIGEN RECEPTORS, COMPOSITIONS, AND METHODS

(71) Applicant: REGENTS OF THE UNIVERSITY OF MINNESOTA, Minneapolis, MN (US)

(72) Inventors: Dan Samuel Kaufman, La Jolla, CA (US); David Lee Lampi Hermanson, San Diego, CA (US); Branden Scott Moriarity, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/546,177

(22) PCT Filed: Jan. 28, 2016

(86) PCT No.: PCT/US2016/015351
§ 371 (c)(1),
(2) Date: Jul. 25, 2017

(87) PCT Pub. No.: WO2016/123333
PCT Pub. Date: Aug. 4, 2016

(65) Prior Publication Data
US 2018/0002438 A1  Jan. 4, 2018

Related U.S. Application Data

(60) Provisional application No. 62/109,281, filed on Jan. 29, 2015.

(51) Int. Cl.
| | |
|---|---|
| C07K 16/28 | (2006.01) |
| C07K 14/705 | (2006.01) |
| C12N 5/16 | (2006.01) |
| A61K 39/00 | (2006.01) |
| C07K 16/30 | (2006.01) |
| A61K 35/17 | (2015.01) |
| C07K 14/47 | (2006.01) |
| C07K 14/54 | (2006.01) |
| C07K 14/725 | (2006.01) |

(52) U.S. Cl.
CPC ............. *C07K 16/30* (2013.01); *A61K 35/17* (2013.01); *C07K 14/4747* (2013.01); *C07K 14/54* (2013.01); *C07K 14/7051* (2013.01); *C07K 14/70578* (2013.01); *C07K 14/70596* (2013.01); *A61K 2039/505* (2013.01); *C07K 2319/02* (2013.01); *C07K 2319/03* (2013.01); *C07K 2319/33* (2013.01); *C07K 2319/40* (2013.01); *C07K 2319/74* (2013.01)

(58) Field of Classification Search
None
See application file for complete search history.

(56) References Cited

U.S. PATENT DOCUMENTS

| | | |
|---|---|---|
| 2009/0196870 A1 | 8/2009 | Ledbetter et al. |
| 2017/0081411 A1* | 3/2017 | Engels .................. C07K 16/00 |
| 2018/0085399 A1* | 3/2018 | Ahmed .................. A61K 35/17 |

FOREIGN PATENT DOCUMENTS

| | | |
|---|---|---|
| EP | 1734119 | 12/2006 |
| JP | 2008/005722 | 1/2008 |
| WO | WO 2005/044996 | * 5/2005 |
| WO | WO 2010/040091 | 4/2010 |
| WO | WO 2013/126729 | 8/2013 |
| WO | WO 2014/153270 | 9/2014 |
| WO | WO 2014/179759 | 11/2014 |
| WO | WO 2015/168613 | 11/2015 |

OTHER PUBLICATIONS

Altvater et al., 2B4 (CD244) signaling via chimeric receptors costimulates tumor-antigen speciWc proliferation and in vitro expansion of human T cells; Cancer Immunol Immunother (2009) 58:1991-2001.*
Li et al Expression of chimeric antigen receptors in natural killer cells with a regulatory-compliant non-viral method; Cancer Gene Therapy (2010) 17, 147-154.*
Dotti et al Design and Development of Therapies using Chimeric Antigen Receptor-Expressing T cells Immunol Rev. Jan. 2014 ; 257(1): pp. 1-35.*
Shimasaki et al., A clinically adaptable method to enhance the cytotoxicity of natural killer cells against B-cell malignancies Cytotherapy, 2012; 14: 830-840.*
Shemesh et al., Splice variants of human natural cytotoxicity receptors: novel innate immune checkpoints Cancer Immunology, Immunotherapy pp. 1-13.*
Chimeric antigen receptor T cell From Wikipedia, the free encyclopedia downloaded Jul. 16, 2019; pp. 1-13.*
Wolan et al., Crystal structure of the murine NK cell—activating receptor NKG2D at 1.95 Å 2001 nature immunology pp. 248-254.*
Dotti et al Design and development of therapies using chimeric antigen receptor-expressing T cells vol. 257, Issue1 Special Issue: Adoptive Immunotherapy for Cancer Jan. 2014 pp. 107-126.*
Abate-Daga et al CAR models: next-generation CAR modifications for enhanced T-cell function Molecular Therapy-Oncolytics, 2016 pp. 1-7.*

(Continued)

*Primary Examiner* — Maria G Leavitt
(74) *Attorney, Agent, or Firm* — Fish & Richardson P.C.; J. Patrick Finn, III

(57) ABSTRACT

This disclosure describes chimeric antigen receptors for expression in a Natural Killer (NK) cell, pharmaceutical compositions that include NK cells (and/or iPSCs) modified to express a chimeric antigen receptor, and methods involving such chimeric antigen receptors. Generally, the chimeric antigen receptor includes an ectodomain that includes an antigen recognition region, a transmembrane domain linked to the ectodomain, and an endodomain linked to the transmembrane domain. The endodomain can include a signaling peptide that activates an NK cell.

7 Claims, 19 Drawing Sheets

(56) References Cited

OTHER PUBLICATIONS

Ahmed et al., "Human Epidermal Growth Factor Receptor 2 (HER2)—Specific Chimeric Antigen Receptor—Modified T Cells for the Immunotherapy of HER2-Positive Sarcoma,"*J Clin Oncol.*, 33(15):1688-1696, May 20, 2015.
Aker et al., "Extended core sequences from the cHS4 insulator are necessary for protecting retroviral vectors from silencing position effects," *Hum Gene Ther.*, 18(4):333-343, Apr. 2007.
Altvater et al., "2B4 (CD244) signaling by recombinant antigen-specific chimeric receptors costimulates natural killer cell activation to leukemia and neuroblastoma cell," *Clinical Canc Res.*, 15(15):4857-4866, Aug. 1, 2009.
Bachanova et al., "Clearance of acute myeloid leukemia by haploidentical natural killer cells is improved using IL-2 diphtheria toxin fusion protein," *Blood.*, 123(25):3855-3863, 2014.
Bachanova., "NK Cells in Therapy of Cancer," *Crit Rev Oncog.*, 19(1-2):133-141, 2014.
Barrett et al., "Chimeric Antigen Receptor Therapy for Cancer," *Annual Rev Med.*, 65:333-347, Jan. 2014.
Beatty et al., "Mesothelin-Specific Chimeric Antigen Receptor mRNA-Engineered T Cells Induce Antitumor Activity in Solid Malignancies," *Canc Immunol Res.*, 2(2):112-120, Feb. 2014.
Bollino and Webb., "Chimeric antigen receptor—engineered natural killer and natural killer T cells for cancer immunotherapy," *Transl Res.*, 187:32-43, Sep. 2017.
Bryant et al., "Calculation of lytic units for the expression of cell-mediated cytotoxicity," *J Immunol Methods.*, 146(1):91-103, 1992.
Bryceson et al., "Activation, coactivation, and costimulation of resting human natural killer cells," *Immunol Rev.*, 214(1):73-91, Dec. 2006.
Burgess-Beusse et al., "The insulation of genes from external enhancers and silencing chromatin," *PNAS.*, 99(suppl 4):16433-16437, Dec. 10, 2002.
Caligiuri., "Human natural killer cells," *Blood.*, 112(3):461-469, Aug. 1, 2008.
Carlsten and Childs, "Genetic manipulation of NK cells for cancer immunotherapy: techniques and clinical implications," *Front Immunol.*, 6(Article 266), 9 pages, Jun. 10, 2015.
Chang et al., "A Chimeric Receptor with NKG2D Specificity Enhances Natural Killer Cell Activation and Killing of Tumor Cells," *Cancer Res.*, 73(6):1777-1786, Mar. 15, 2013.
Cheng et al., "NK cell-based immunotherapy for malignant diseases," *Cell Mol Immunol.*, 10:230-252, 2013.
Childs and Carlsten., "Therapeutic approaches to enhance natural killer cell cytotoxicity against cancer: the force awakens," *Nat Rev Drug Disc.*, 14:487-498, 2015.
Chowdhury et al., "Isolation of a high-affinity stable single-chain Fv specific for mesothelin from DNA-immunized mice by phage display and construction of a recombinant immunotoxin with anti-tumor activity," *PNAS.*, 95(2):669-674, Jan. 20, 1998.
Denman et al., "Membrane-Bound IL-21 Promotes Sustained Ex Vivo Proliferation of Human Natural Killer Cells," *Plos One.*, 7(1):e30264, Jan. 2012.
Dhar and Wu et al., "NKG2D and its ligands in cancer," *Curr Opinion Immunol.*, 51:55-61, Apr. 2018.
Dolstra et al., "Successful Transfer of Umbilical Cord Blood CD34+ Hematopoietic Stem and Progenitor-derived NK Cells in Older Acute Myeloid Leukemia Patients," *Clin Cancer Res.*, 23(15):4107-4118, Aug. 2017.
Eagle and Trowsdale., "Promiscuity and the single receptor: NKG2D," *Nat Rev Immunol.*, 7:737-744, 2007.
European Office Action in European Application No. EP16704526.9, dated May 2, 2018, 6 pages.
Fesnak et al., "Engineered T cells: the promise and challenges of cancer immunotherapy," *Nat Rev Canc.*, 16:566-581, 2016.

Figueroa et al., "Chimeric Antigen Receptor Engineering: A Right Step in the Evolution of Adoptive Cellular Immunotherapy," *Int Rev Immunol.*, 34(2):154-187, 2015.
Garrity et al., "The activating NKG2D receptor assembles in the membrane with two signaling dimers into a hexameric structure," *PNAS.*, 102(21):7641-7646, May 24, 2005.
Geller et al., "A phase II study of allogeneic natural killer cell therapy to treat patients with recurrent ovarian and breast cancer," *Cytotherapy.*, 13(1):98-107.
Giudice and Trounson., "Genetic Modification of Human Embryonic Stem Cells for Derivation of Target Cells," *Cell Stem Sell.*, 2(5):422-433, May 8, 2008.
Grupp et al., "Chimeric Antigen Receptor—Modified T Cells for Acute Lymphoid Leukemia," *N Engl J Med.*, 368:1509-1518, Apr. 18, 2013.
Guillerey et al., "Targeting natural killer cells in cancer immunotherapy," *Nat Immunol.*, 17:1025-1036, 2016.
Handgretinger et al., "Exploitation of natural killer cells for the treatment of acute leukemia," *Blood.*, 127:3341-3349, Jun. 30, 2016.
Hassan and Ho., "Mesothelin targeted cancer immunotherapy," *Euro J Canc.*, 44(1):46-53, Jan. 2008.
Hermanson and Kaufman., "Utilizing chimeric antigen receptors to direct natural killer cell activity," *Front. Immunol.*, 6(Article 195), 6 pages, Apr. 28, 2015.
Hermanson et al., "Induced Pluripotent Stem Cell-Derived Natural Killer Cells for Treatment of Ovarian Cancer," *Stem Cells.*, 34(1):93-101, Jan. 2016.
Ho et al., "Costimulation of Multiple NK Cell Activation Receptors by NKG2D," *J Immunol.*, 169(7):3667-3675 Oct. 1, 2002.
Imai et al., "Genetic modification of primary natural killer cells overcomes inhibitory signals and induces specific killing of leukemic cells," *Blood.*, 106:376-383, 2005.
International Preliminary Report on Patentability in International Application No. PCT/US2015/022998, dated Oct. 4, 2016, 6 pages.
International Search Report and Written Opinion in International Application No. PCT/US2015/022998, dated Oct. 1, 2015, 9 pages.
Klingemann et al., "Natural Killer Cells for Immunotherapy—Advantages of the NK-92 Cell Line over Blood NK Cells," *Front Immunol.*, 7(Article 91), 7 pages, Mar. 14, 2016.
Knorr et al., "Clinical-Scale Derivation of Natural Killer Cells From Human Pluripotent Stem Cells for Cancer Therapy," *Stem Cells Transl Med.*, 2(4):274-283, 2013.
Knorr et al., "Engineered Human Embryonic Stem Cell-Derived Lymphocytes to Study In Vivo Trafficking and Immunotherapy," *Stem Cells and Development.*, 22(13) Jul. 2013.
Koehl et al., "Advances in clinical NK cell studies: Donor selection, manufacturing and quality control," *OncoImmunology*, 5:4, Article e1115178, 2015, 12 pages.
Koneru et al., "IL-12 secreting tumor-targeted chimeric antigen receptor T cells eradicate ovarian tumors in vivo," *OncoImmunology.*, 4:3, Article e994446, 2015, 12 pages.
Kwon et al., "Stepwise phosphorylation of p65 promotes NF-κB activation and NK cell responses during target cell recognition," *Nature Comm.*, 7(Article No. 11686), 2016, 15 pages.
Lanier et al., "Co-association of CD3ζ with a receptor (CD16) for IgG Fc on human natural killer cells," *Nature.*, 342:803-805, Dec. 14, 1989.
Lanier., "Up on the tightrope: natural killer cell activation and inhibition," *Nature Immunology.*, 9:495-502, 2008.
Li et al., "Human iPSC-derived natural killer cells engineered with chimeric antigen receptors enhance anti-tumor activity," *Cell Stem Cell.*, 23:181-192, 2018.
Liu et al., "Cord blood NK cells engineered to express IL-15 and a CD19-targeted CAR show long-term persistence and potent antitumor activity," *Leukemia.*, 32:520-531, 2018.
Long et al., "Controlling Natural Killer Cell Responses: Integration of Signals for Activation and Inhibition," *Annual Rev Immunol.*, 31:227-258, 2013.
Long., "Negative signaling by inhibitory receptors: the NK cell paradigm," *Immunol Rev.*, 224(1):70-84, Aug. 2008.

(56) References Cited

OTHER PUBLICATIONS

Love and Hayes., "ITAM-mediated Signaling by the T-Cell Antigen Receptor," *Cold Spring Harb Perspect Biol.*, 2:a002485, 2010, 12 pages.

Maude et al., "CD19-targeted chimeric antigen receptor T-cell therapy for acute lymphoblastic leukemia," *Blood.*, 125(26):4017-4023, Jun. 25, 2015.

Miller et al., "Successful adoptive transfer and in vivo expansion of human haploidentical NK cells in patients with cancer," *Blood.*, 105(8):3051-3057, 2005.

Moriarity et al., "Modular assembly of transposon integratable multigene vectors using RecWay assembly," *Nucleic Acids Res.*, 41(8):e92, Apr. 1, 2013.

Morvan and Lanier., "NK cells and cancer: you can teach innate cells new tricks," *Nat Rev Cancer.*, 16:7-19, 2016.

Nakajima et al., "Activating interactions in human NK cell recognition: the role of 2B4-CD48," *Eur J Immunol.*, 29(5):1676-1683, May 1999.

Ng et al., "A protocol describing the use of a recombinant protein-based, animal product-free medium (APEL) for human embryonic stem cell differentiation as spin embryoid bodies," *Nature Protocols.*, 3:768-776, 2008.

Ni et al., "Expression of chimeric receptor CD244 by natural killer cells derived from human pluripotent stem cells improves in vitro activity but does not enhance suppression of HIV infection in vivo," *Stem Cells.*, 32(4):1021-1031, 2014.

Ni et al., "Hematopoietic and Nature Killer Cell Development from Human Pluripotent Stem Cells," *Embryonic Stem Cell Immunobiol.*, 33-41, 2013.

Ni et al., "Human Pluripotent Stem Cells Produce Natural Killer Cells That Mediate Anti-HIV-1 Activity by Utilizing Diverse Cellular Mechanisms," *J Virology.*, 85(1):43-50, Jan. 2011.

Porter et al., "Chimeric Antigen Receptor-Modified T Cells in Chronic Lymphoid Leukemia," *N. Engl J Med.*, 365:725-733, 2011.

Qasim et al., "Molecular remission of infant B-ALL after infusion of universal TALEN gene-edited CAR T cells," *Sci Transl Med.*, 9(374):eaaj2013, Jan. 25, 2017.

Ramos et al., "CAR-T Cell Therapy for Lymphoma," *Annu Rev Med.*, 67:165-183, 2016.

Romee et al., "Cytokine-induced memory-like natural killer cells exhibit enhanced responses against myeloid leukemia," *Sci Transl Med.*, 8(357):357ra123, Sep. 21, 2016.

Rosen et al., "A Structural Basis for the Association of DAP12 with Mouse, but Not Human, NKG2D," *J Immunol.*, 173(4):2470-2478, Aug. 15, 2004.

Sakamoto et al., "Phase I clinical trial of autologous NK cell therapy using novel expansion method in patients with advances digestive cancer," *J Transl Med.*, 13:277, Aug. 25, 2015.

Sentman et al., "NKG2D CARs as cell therapy for cancer," *Cancer J.*, 20(2):156-159, Mar./Apr. 2014.

Sivori et al., "2B4 functions as a co-receptor in human NK cell activation," *Eur J Immunol.*, 30(3):787-793, 2000.

Smyth et al., "Activation of NK cell cytotoxicity," *Mol Immunol.*, 42(4):501-510, Feb. 2005.

Song et al., "Chimeric NKG2D CAR-Expressing T Cell-Mediated Attack of Human Ovarian Cancer Is Enhanced by Histone Deacetylase Inhibition," *Hum Gene Ther.*, 24(3):295-305, Mar. 2013.

Song et al., "In Vivo Persistence, Tumor Localization, and Antitumor Activity of CAR-Engineered T Cells Is Enhanced by Costimulatory Signaling through CD137 (4-1BB)," *Cancer Res.*, 71(13):4617-4627, Jul. 2011.

Teachey et al., "Identification of Predictive Biomarkers for Cytokine Release Syndrome after Chimeric Antigen Receptor T-cell Therapy for Acute Lymphoblastic Leukemia," *Canc Disc.*, 6(6):664-679, Jun. 2016.

Themeli et al., "New Cell Sources for T Cell Engineering and Adoptive Immunotherapy," *Cell Stem Cell.*, 16(4):357-366, Apr. 2, 2015.

Topfer et al., "DAP12-Based Activating Chimeric Antigen Receptor for NK Cell Tumor Immunotherapy," *J Immunol.*, 194(7):3201-3212, Apr. 1, 2015.

Vivier et al., "Natural Killer Cell Signaling Pathways," *Science.*, 306(5701):1517-1519, Nov. 26, 2004.

Wilber et al., "Efficient and Stable Transgene Expression in Human Embryonic Stem Cells Using Transposon-Mediated Gene Transfer," *Stem Cells.*, 25(11):2919-2927, Nov. 2007.

Woll et al., "Human Embryonic Stem Cell-Derived NK Cells Acquire Functional Receptors and Cytolytic Activity," *J Immunol.*, 175(8):5095-5103, Oct. 15, 2005.

Woll et al., "Human embryonic stem cells differentiate into a homogeneous population of natural killer cells with potent in vivo antitumor activity," *Blood.*, 113(24):6094-6101, 2009.

Xie et al., "Seamless gene correction of β-thalassemia mutations in patient-specific iPSCs using CRISPR/Cas9 and piggyBac," *Genome Res.*, 24:1526-1533, 2014.

Yahata et al., "cHS4 Insulator-mediated Alleviation of Promoter Interference during Cell-based Expression of Tandemly Associated Transgenes," *J Mol Biol.*, 374(3):580-590, Nov. 30, 2007.

Yang et al., "Phase I Study of Random Healthy Donor—Derived Allogeneic Natural Killer Cell Therapy in Patients with Malignant Lymphoma or Advanced Solid Tumors," *Canc Immunol Res.*, 4(3):215-224, Mar. 2016.

Zhang and Sentman., "Cancer Immunotherapy Using a Bispecific NK Receptor Fusion Protein that Engages both T Cells and Tumor Cells," *Canc Res.*, 71(6): Mar. 2011.

Zhang et al., "Interplay between hepatitis C virus and ARF4," *Virol Sinica.*, 32(6):533-536, Dec. 2017.

Geller and Miller., "Use of allogeneic NK cells for cancer immunotherapy," Immuno Ther., 3(12):1445-1459, Dec. 2011.

Geller et al., "A phase II study of allogeneic natural killer cell therapy to treat patients with recurrent ovarian and breast cancer," Cytotherapy, 13(1):98-107, Jan. 2011.

Japanese Office action in Japanese Application No. 2017-540182 dated Oct. 23, 2019, 13 pages (with English translation).

Wu et al., "DNAM-1-based chimeric antigen receptors enhance T cell effector function and exhibit in vivo efficacy against melanoma," Cancer Immunology, Immunotherapy, 64(4):409-18, Apr. 2015.

Zhang et al., "Generation of antitumor responses by genetic modification of primary human T cells with a chimeric NKG2D receptor," Cancer Research, 66(11):5927-33, Jun. 2006.

\* cited by examiner

A

| Receptor (*Ligand*) | Degranualtion | Polarization | Killing |
|---|---|---|---|
| NKG2D (*ULBP1*) | No | No | No |
| 2B4 (*CD48*) | No | No | No |
| NKG2D + 2B4 | Yes[a] | No | No |
| LFA-1 (*ICAM-1*) | No | Yes[b] | No |
| NKG2D + 2B4 + LFA-1 | Yes | Yes | Yes |
| CD16 (*anti-S2 IgG*) | Yes | No | No |
| CD16 + LFA-1 | Yes | Yes | Yes |

B

| Receptor | Signaling Adaptor | Signaling Motif |
|---|---|---|
| CD16 or NKp46 | CD3ζ or FcRγ | Function as dimers; CD3ζ uses 3 ITAMs; FcRγ has 1 ITAM |
| NKp44 | DAP12 | Homodimer; 1 ITAM |
| NKG2D | DAP10 | YxxM Motif |
| 2B4 | None | Contains 4 ITSMs |

C

FIG. 2
A
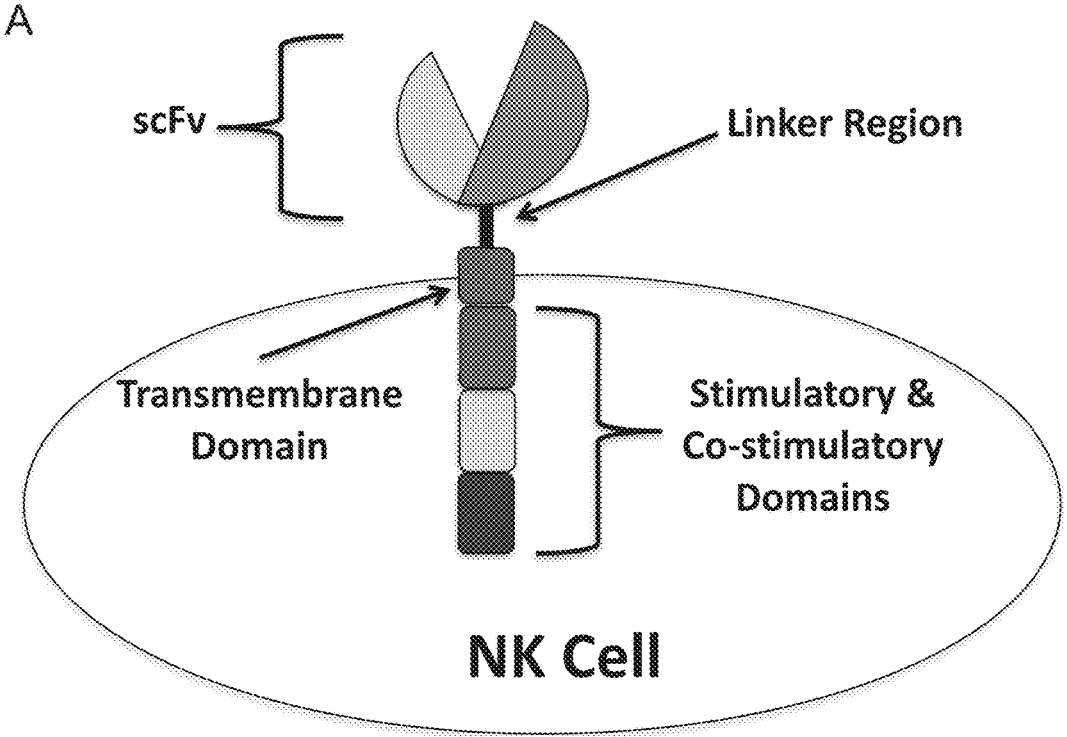
B
CAR 1
CAR 2
CAR 3
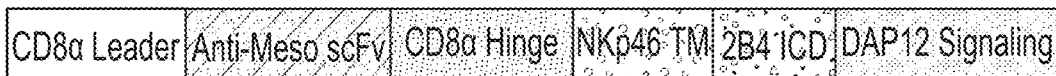
CAR 4
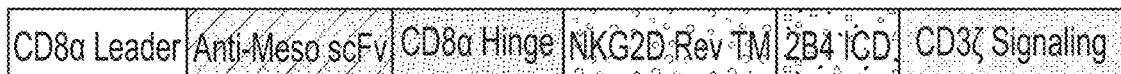

CAR5 (NKG2D/41BB/CD3)

| CD8α Leader | Anti-Meso scFv | CD8α Hinge | NKG2D Rev TM | 41BB ICD | CD3ζ |

CAR6 (NKG2D/2B4/DAP12/CD3)

| CD8α Leader | Anti-Meso scFv | CD8α Hinge | NKG2D Rev TM | 2B4 ICD | DAP12 | CD3ζ |

CAR7 (NKG2D/2B4/DAP10/CD3)

| CD8α Leader | Anti-Meso scFv | CD8α Hinge | NKG2D Rev TM | 2B4 ICD | DAP10 | CD3ζ |

CAR8 (NKG2D/IL21R/CD3)

| CD8α Leader | Anti-Meso scFv | CD8α Hinge | NKG2D Rev TM | IL21R ICD | CD3ζ |

CAR9 (NKG2D/41BB/2B4/CD3)

| CD8α Leader | Anti-Meso scFv | CD8α Hinge | NKG2D Rev TM | 41BB ICD | 2B4 ICD | CD3ζ |

FIG. 6

Note: lytic units were calculated as the number of effector cells required to lyse 20% of $2 \times 10^3$ target cells.
* indicated $P<0.01$.

CHIMERIC ANTIGEN RECEPTORS, COMPOSITIONS, AND METHODS

CROSS-REFERENCE TO RELATED APPLICATION

This application is the § 371 U.S. National Stage of International Application No. PCT/US2016/015351, filed 28 Jan. 2016, which claims priority to U.S. Provisional Patent Application Ser. No. 62/109,281, filed Jan. 29, 2015, each of which is incorporated herein by reference.

SUMMARY

This disclosure describes, in one aspect, a chimeric antigen receptor for expression in a Natural Killer (NK) cell. Generally, the chimeric antigen receptor includes an ectodomain that includes an antigen recognition region, a transmembrane domain linked to the ectodomain, and an endodomain linked to the transmembrane domain. The endodomain can include a signaling peptide that activates an NK cell.

In some embodiments, the antigen recognition domain can specifically bind an antigen associated with a disease.

In some embodiments, the antigen recognition domain can specifically bind a tumor antigen.

In some embodiments, the ectodomain can further include a signal peptide or leader sequence and/or a spacer.

In some embodiments, the endodomain can include a signaling domain of and NK cell membrane-bound signaling adaptor protein such as, for example, 2B4, DAP10, DAP12, IL21R, CD137 (41BB), or CD3ζ.

In some embodiments, the transmembrane domain can include a transmembrane region of a natural cytotoxicity receptor expressed in NK cells such as, for example, CD16, NKp44, NKp46, or NKG2D.

In another aspect, this disclosure describes a pharmaceutical composition that includes an NK cell (and/or iPSCs) modified to express any embodiment of chimeric antigen receptor summarized above.

In another aspect, this disclosure describes a method of providing immunotherapy to a subject having a condition. Generally, the method includes administering to the subject the therapeutic composition summarized above in which the antigen recognition region of the chimeric antigen receptor specifically binds to an antigen associated with the condition.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2. (A) A generalized schematic illustration of an NK-activating CAR. (B) Schematic of novel chimeric antigen receptor constructs. Chimeric antigen receptors were cloned into a pkt2 vector containing an IR/DR for use with SB100X transposase, a mCAGs promoter, chimeric antigen receptor (CAR) sequence, Internal ribosomal entry site (IRES), and GFP:Zeo selection marker. Chimeric antigen receptor fragments were obtained from UniProt and assembled through gBlock synthesis and traditional restriction enzyme cloning (IDT).

FIG. 6. Exemplary additional NK-activating chimeric antigen receptors.

DETAILED DESCRIPTION OF ILLUSTRATIVE EMBODIMENTS

Figure 1:
FIG. 1. (A) Exemplary natural cytotoxicity receptors and the effect of binding those receptors with their ligands on NK cell degranulation and polarization and target cell killing. (B) Representative examples of natural cytotoxicity receptors and their corresponding signaling adaptors. (C) Third generation chimeric T cell antigen receptor construct used in iPSC-derived NK cells.

This disclosure describes chimeric antigen receptors designed to specifically incorporate NK cell activation domains. Chimeric antigen receptors can incorporate intracellular and/or transmembrane regions including, for example, intracellular and/or transmembrane regions from CD16, NKp44, NKp46, and/or NKG2D, linked to co-activation or signaling domains from, for example, 2B4 (CD244), CD137 (41BB), IL21, DAP10, DAP12, and/or CD3ζ.

Chimeric antigen receptors (CARs) are engineered artificial receptors that can provide an engineered specificity to an immune cell that expresses the CAR. Generally, an immune cell population can be collected from a subject that has a particular form of cancer. The collected immune cells can be modified to express a chimeric antigen receptor that specifically binds to antigens expressed by tumor cells, then reintroduced into the subject. The modified immune cells that express the chimeric antigen receptor are better able to recognize and kill tumor cells that express the antigen(s) specifically recognized by the chimeric antigen receptor.

Chimeric antigen receptors have been designed to activate T cells for the treatment of refractory ALL (targeting CD19), pancreatic cancer (targeting mesothelin), and other malignancies. Several chimeric antigen receptors constructs exist, but most were designed to activate T cells.

In contrast, the chimeric antigen receptors described herein are designed to be expressed in induced pluripotent stem cells (iPSCs), which can then be differentiated into NK cells. They also can be expressed directly into peripheral blood (PB)-NK cells, NK-92 cells, or another suitable NK cell line. NK-92 cells or other NK cell lines have been used in clinical studies for anti-cancer therapy. NK cells that express the chimeric antigen receptor can then be used as an immunotherapy for the treatment of multiple cancers. The chimeric antigen receptors described herein can include a signaling domain that could be used with antigen-recognition portions of various targeting antibodies. Specifically, this disclosure describes exemplary embodiments that reflect mesothelin-targeted chimeric antigen receptors for the treatment of ovarian cancer. The described embodiments can have broader utility, however, since mesothelin is expressed on many adenocarcinomas. Moreover, the described mesothelin targeting domain is merely exemplary; other single chain variable fragments (scFVs) can be engineered into the NK-specific chimeric antigen receptor (NK-CAR) signaling constructs to target essentially any malignancy.

One feature of the NK cell chimeric antigen receptors described herein is that one can bypass the adaptor molecules/accessory proteins that natural cytotoxicity receptors need to initiate signal transduction. Alternatively, or additionally, including the transmembrane domain of receptors that typically associate with an adaptor molecule/accessory protein can allow accessory proteins to bind as well, making signal transduction more likely to be initiated. The NK cell chimeric antigen receptors designed to include, for example, CD3ζ can allow bypassing other natural cytotoxicity receptors. Incorporating the transmembrane domains and other intracellular domains can allow these NK cell chimeric antigen receptors to associate with adaptor proteins and provide improved signaling over CD3ζ alone through activation of multiple pathways.

While some T cell chimeric antigen receptor constructs can activate NK cells to some degree due to shared signaling domains, the chimeric antigen receptors described herein are specifically designed to activate NK cells. Chimeric antigen receptors designed to specifically activate NK cells can improve NK function and receptor utility in NK cell immunotherapy such as, for example, cell-mediated killing of refractory tumors.

A chimeric antigen receptor typically includes an ectodomain, a transmembrane domain, and an endodomain. The endodomain typically resides in the cytoplasm of the cell. Once an antigen is recognized by the ectodomain, the endodomain transmits an activation signal to the NK cell that induces the NK cell to destroy the targeted tumor cell. Exemplary signaling endodomains include, for example, the signaling domains of membrane-bound signaling adaptor proteins, including, for example, 2B4 (CD244), CD137 (41BB), IL21, DAP10, DAP12, and/or CD3ζ, or a portion thereof including, for example, an immunoreceptor tyrosine-based activation motif (ITAMs), a YxxM motif, a TxYxxV/I motif, FcRγ, NKp80 (signaling through an atypical hemi-ITAM), and/or DNAM, etc.

The transmembrane domain traverses the plasma membrane and links the endodomain to the ectodomain. Exemplary transmembrane domains include, for example, the intracellular and/or transmembrane domains of natural cytotoxicity receptors (NCRs) including for example, CD16, NKp44, NKp46, NKG2D, NKp30, NKp80, and/or DNAM-1, or a portions thereof including, for example, one or more charged amino acids. In some embodiments, the charged amino acid can be a lysine and/or an arginine residue. In some cases, a transmembrane region may be from a transmembrane protein, meaning that it natively has an extracellular C-terminal rather than an extracellular N-terminal. In such cases, one can reverse the orientation of the transmembrane region, indicated in, for example, FIG. 6 as "Rev TM" so that the chimeric antigen receptor orients properly in the NK cell membrane.

The ectodomain generally includes a signal peptide and an antigen recognition region. In many embodiments, the ectodomain also can include a spacer. The signal peptide directs the nascent polypeptide into the endoplasmic reticulum so that it can be properly glycosylated and anchored into the plasma membrane. Generally, any eukaryotic signal peptide can be used so long as it directs the protein to the endoplasmic reticulum. One exemplary signal peptide includes the CD8α leader sequence, but other signal peptide sequences may be suitable. The spacer, when present, links the antigen recognition domain to the transmembrane domain. The spacer typically offers flexibility so that antigen recognition region is free to orient in different directions, thereby allowing the antigen recognition region to bind to antigen targets. One exemplary spacer includes the CD8α hinge sequence, but other Ig hinge regions may be suitable. The antigen recognition region can include any peptide sequence that is capable of specifically binding to a designated target. As used herein, "specifically bind" and variations thereof refer to having a differential or a non-general affinity, to any degree, for a particular target. Thus, the antigen recognition region can include a fragment of an antibody such as, for example, an scFv or a Fab that specifically binds to a particular antigen such as, for example, a tumor antigen, a viral antigen, a modified self-antigen, etc. In some embodiments, the scFv can be from a monoclonal antibody. A chimeric antigen receptor can be designed to include an antigen recognition region that can specifically bind to any designated target. Thus, while FIG. 2, FIG. 6, FIG. 7, and FIG. 8 show embodiments that are designed to specifically bind to mesothelin, an NK-activating chimeric antigen receptor can be designed to specifically bind, and therefore target, any antigen associated with cells that are intended to be the target of NK cell-mediated killing including, for example, tumorigenic or virally infected cells. For example, NK cells and/or CARs have demonstrated activity against diverse solid tumors and virally-infected cells including but limited to HIV (human immunodeficiency virus), hepatitis B, hepatitis C, CMV (cytomegalovirus), EBV (Epstein-Barr virus), HPV (human papilloma virus), and others.

Figure 3:
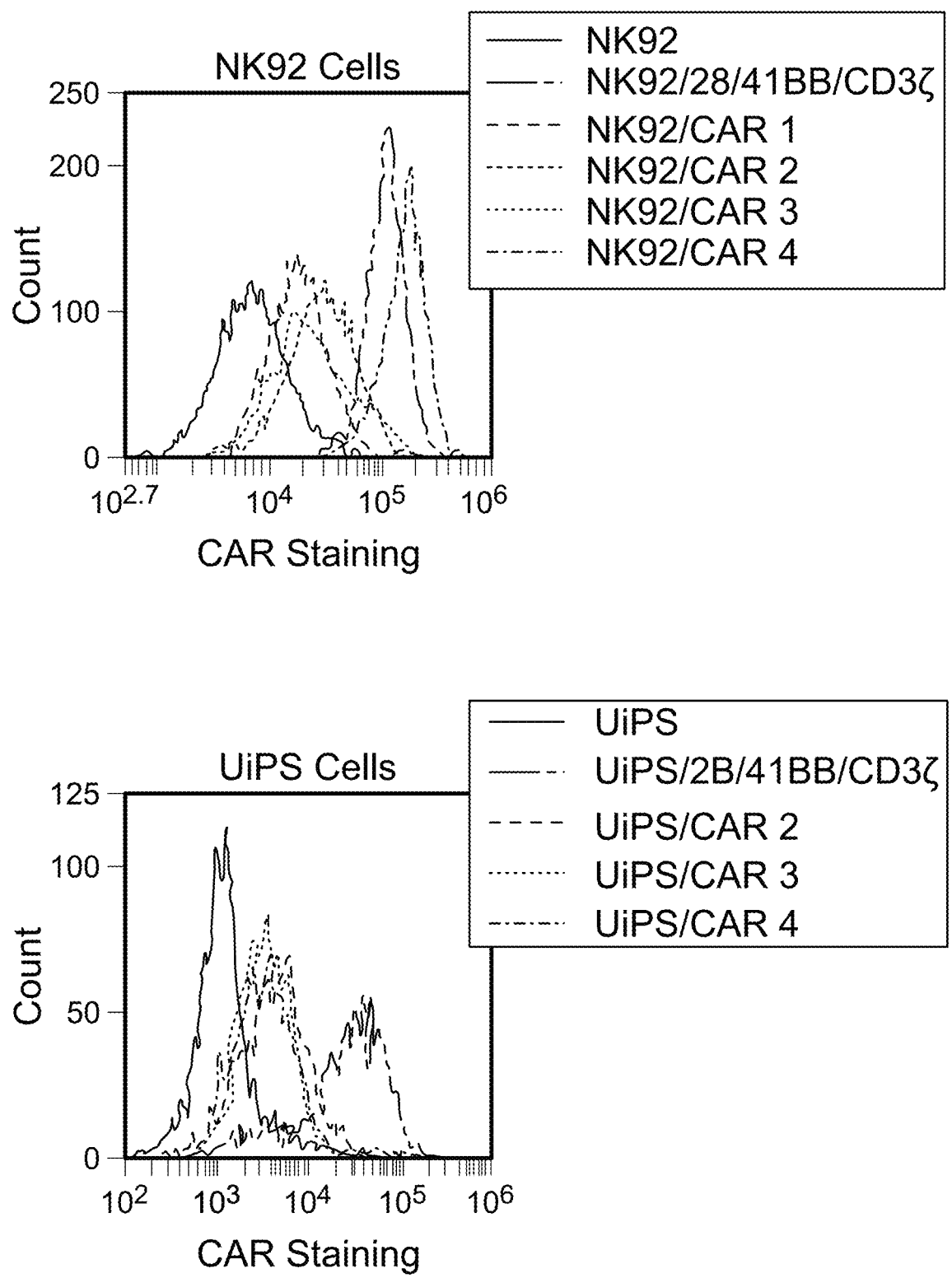
FIG. 3. Surface expression of chimeric antigen receptors in NK92 and iPS cells. NK92 cells or iPS cells were transfected using the Sleeping Beauty transposon system using SB100X. Cells were then selected using Zeocin and flow cytometry was performed to assess cell surface expression of the various chimeric antigen receptors. Expression was assessed using a biotin-conjugated polyclonal goat anti-mouse antibody recognizing the mouse IgG F(ab')2 fragment (Jackson ImmunoResearch Laboratories, Inc., West Grove, Pa., cat #115-065-072). Bound antibody was detected using strepavadin conjugated to a fluorescent dye.

So, for example, to better mediate NK cell cytotoxicity against tumors that include cells that express mesothelin (e.g., ovarian cancers, pancreatic cancers, lung cancers, colon adenocarcinomas, mesotheliomas, and other adenocarcinomas that express mesothelin), a chimeric antigen receptor such as ones shown in FIG. 2, FIG. 6, FIG. 7, and FIG. 8 may be designed and expressed in NK cells. The illustrated chimeric antigen receptor constructs contain an NK cell-specific transmembrane domain and activating domains, and was capable of being expressed in the NK cell tumor line, NK92. Transmembrane and intracellular regions were taken from CD16, NKp44, NKp46, and/or NKG2D, while the activating domains of 2B4, DAP10, DAP12, and/or CD3ζ were combined in a fashion intended to maximally activate NK cells. FIG. 3 shows that NK92 and iPS cells expressed the chimeric antigen receptors shown in FIG. 2.

Figure 4:
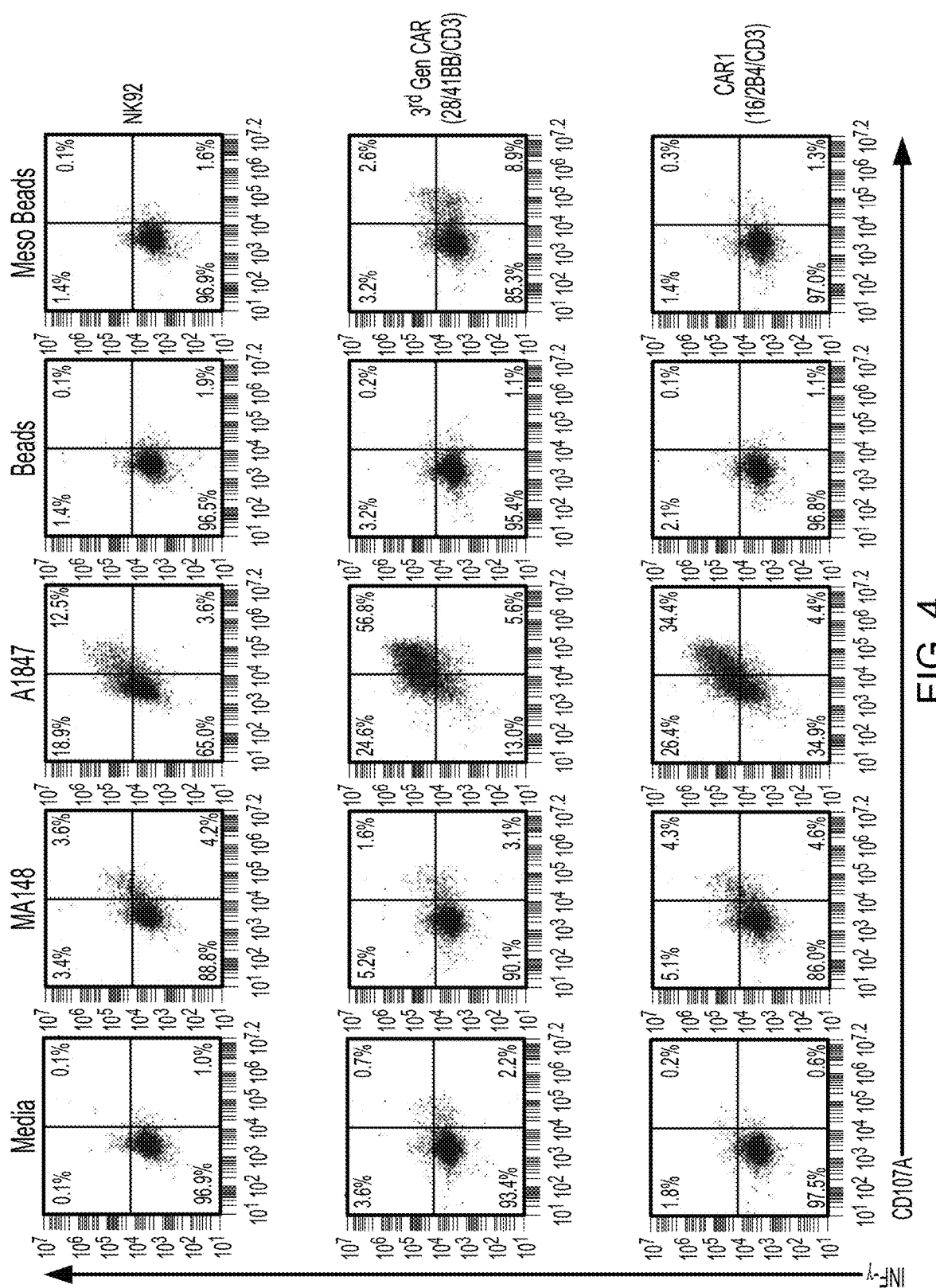
FIG. 4. CD107A release and IFN-γ production in NK92 Cells. NK92 cell degranulation and cytokine production were evaluated by flow cytometry. NK92 cells were mixed 1:1 with mesothelin negative (MA148), mesothelin positive (A1847) ovarian cancer target cells, or Protein A beads with or without conjugation to a mesothelin/Fc chimeric protein. Cells were stained for CD107a and intracellular staining was performed for IFN-γ production.
Figure 4:
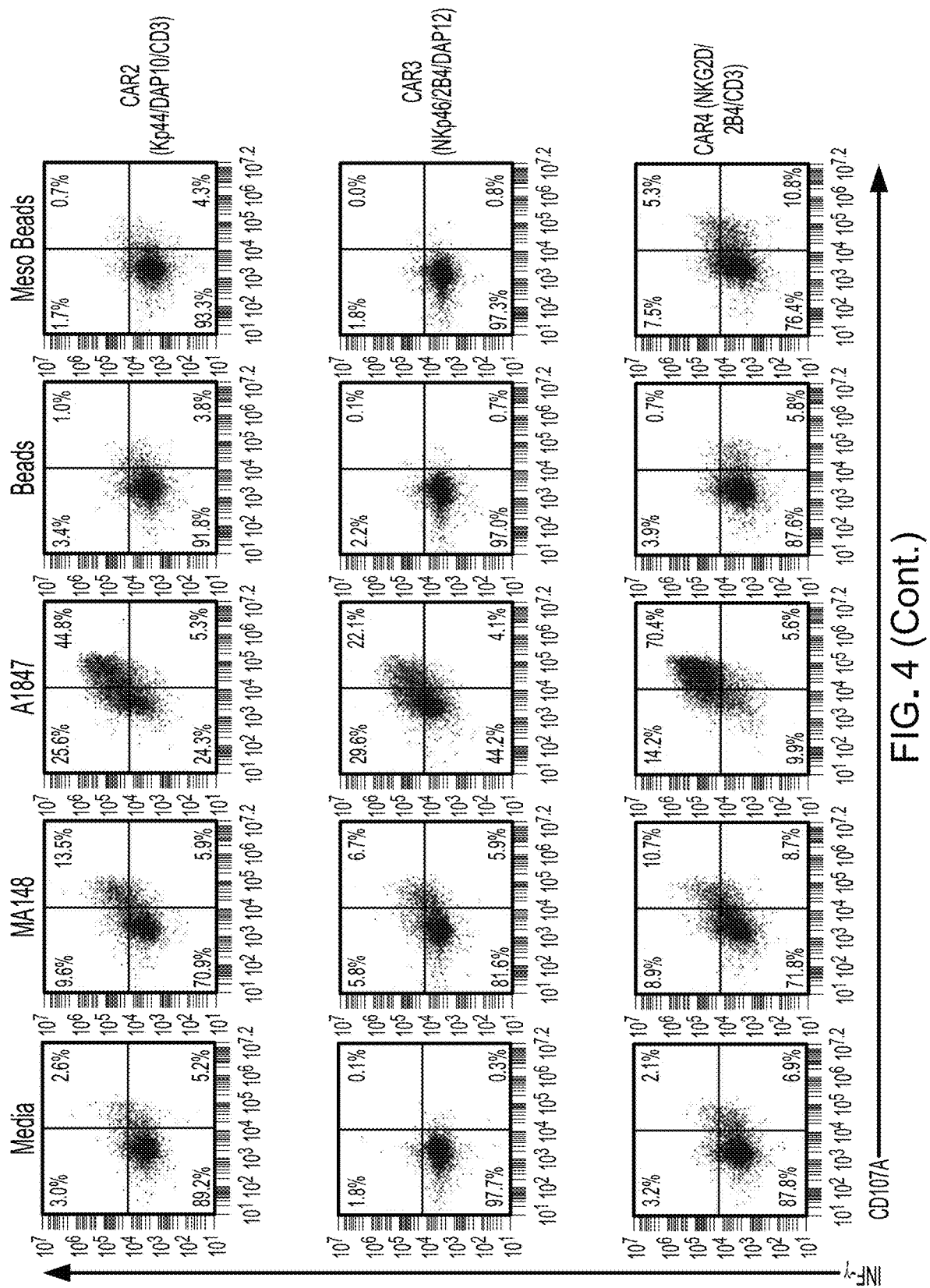

To assess the function of the chimeric antigen receptors, NK cells expressing the chimeric antigen receptors were tested against antigen-coated beads and mesothelin-expressing cell lines. FIG. 4 shows that the chimeric antigen receptors of FIG. 2 enhanced degranulation and cytokine production of NK cells when NK cells expressing the chimeric antigen receptors were mixed with mesothelin-positive targets.

Figure 5:
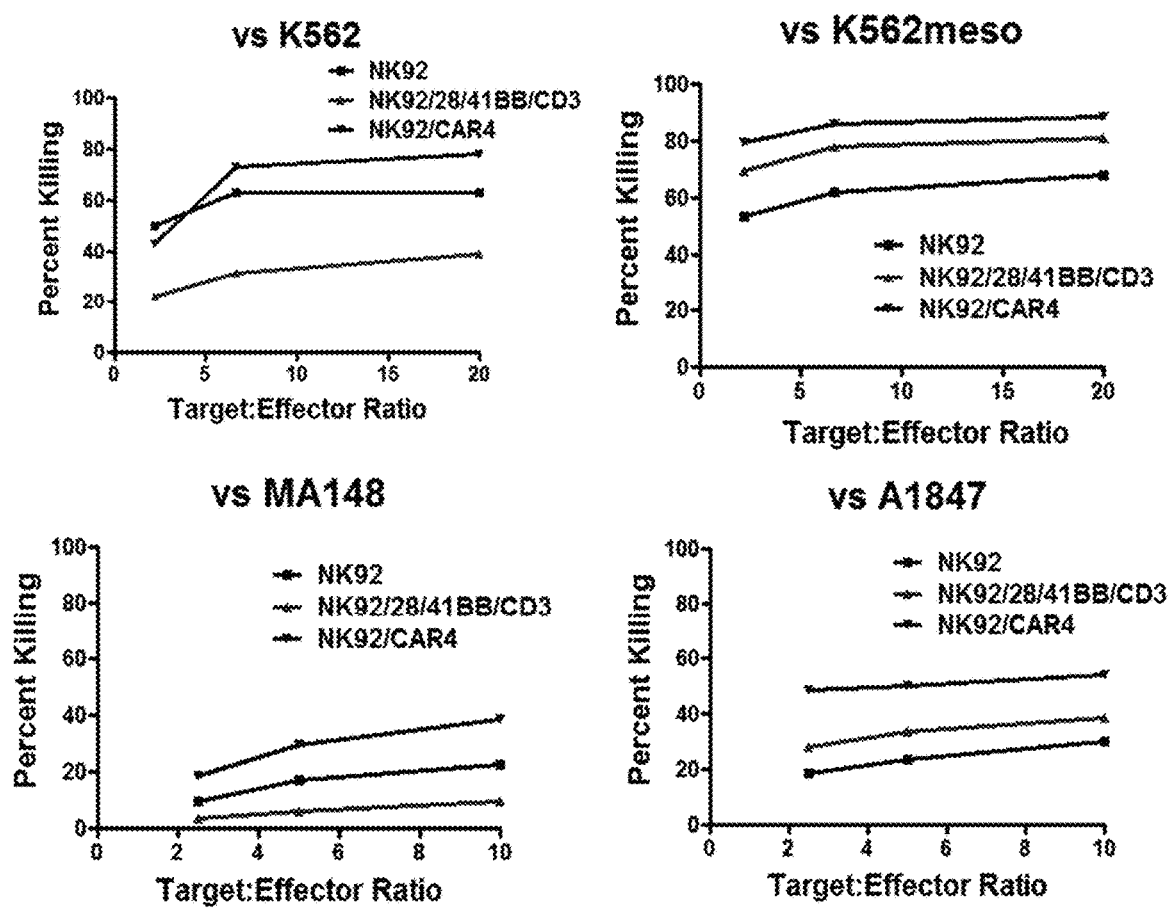
FIG. 5. Cr-51 release assay using NK92 cells. NK92, NK92/28/41BB/CD3, or NK92/CAR4 cells were incubated for 4 hours at the indicated ratios with K562, K562 mesothelin+, MA148, or A1847 cells. Cr-51 release was then detected to evaluate cell killing. This experiment performed as in Woll et al., 2009, *Blood* 113(24):6094-6101, except that iPSC-derived NK cells were used in place of hESC-derived NK cells.
Figure 7:
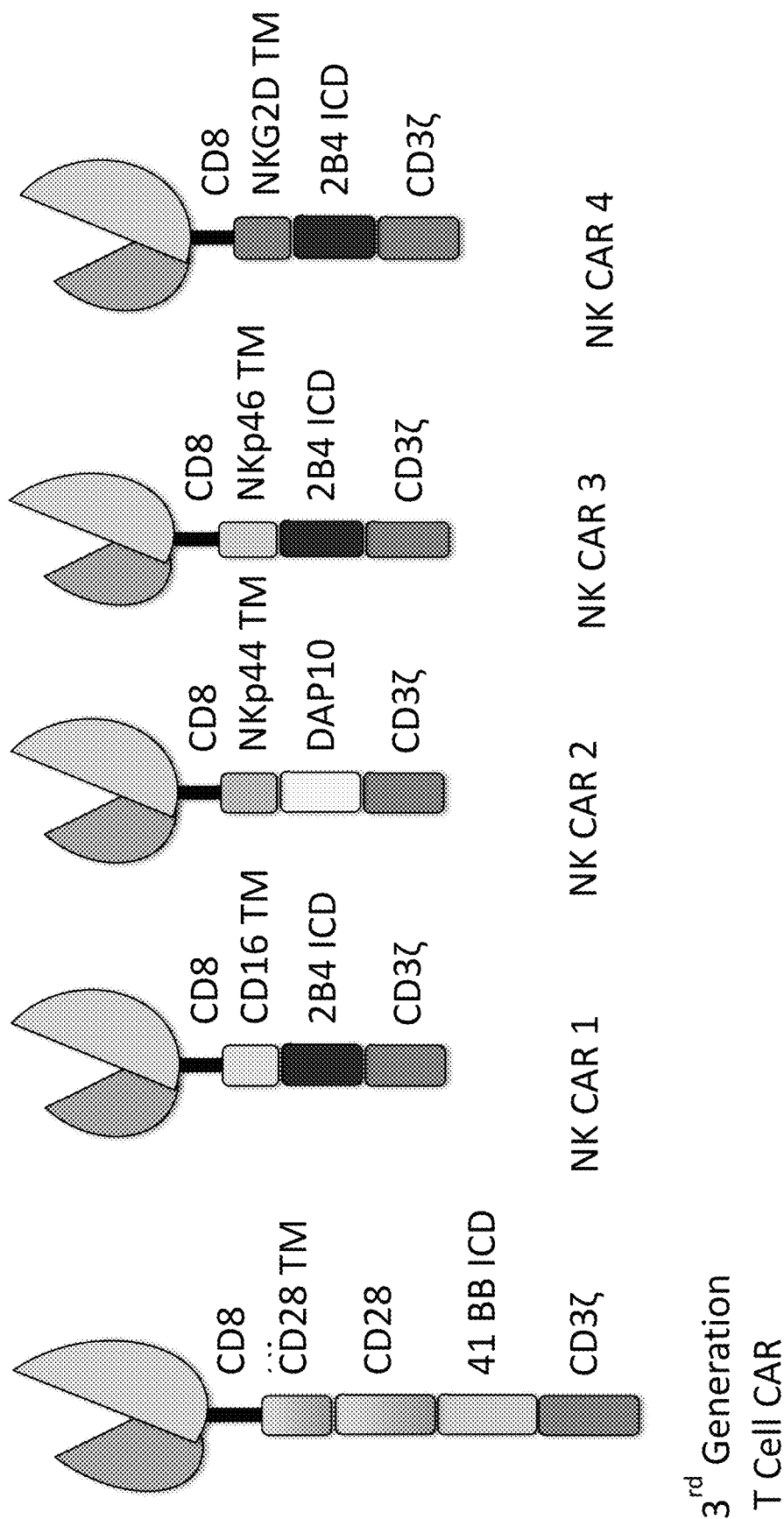
FIG. 7. Schematic illustration comparing a $3^{rd}$ Generation T cell CAR with exemplary NK CAR constructs reflected in FIG. 2.
Figure 8:
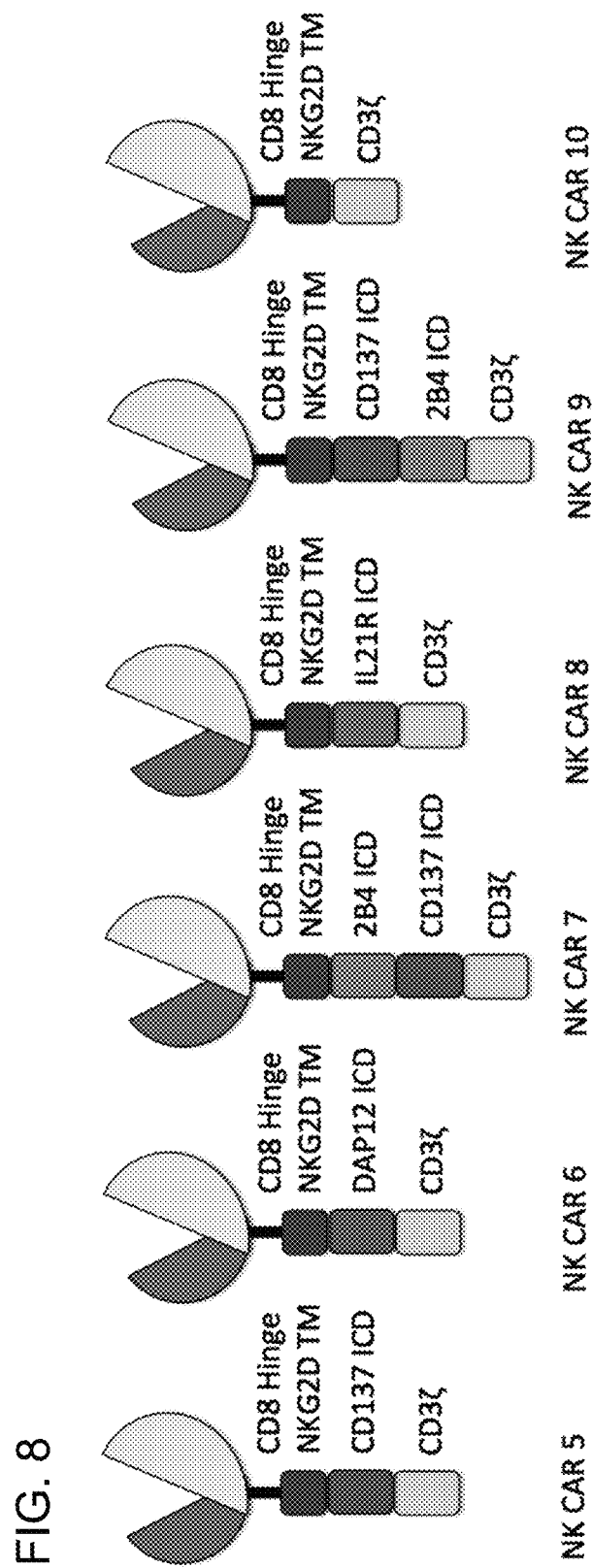
FIG. 8. Schematic illustration of exemplary NK CAR constructs.

FIG. 5 shows that NK92 cells expressing an NK-specific chimeric antigen receptor as described herein improved in vitro killing of mesothelin-positive target cells compared to a third generation T cell-specific chimeric antigen receptor (NK92/28/41BB/CD3ζ) or non-transfected NK92 cells.

Figure 9:
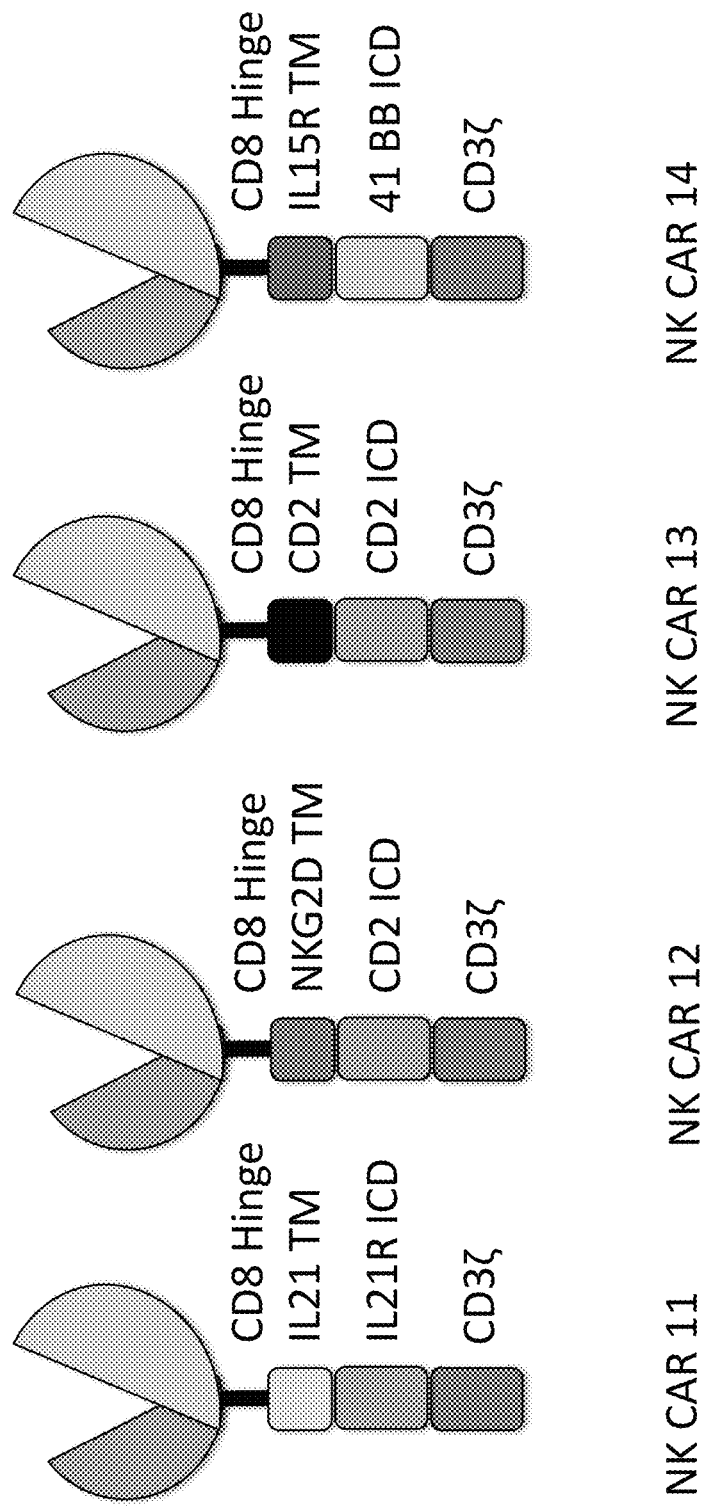
FIG. 9. Schematic illustration of exemplary NK CAR constructs.
Figure 10:
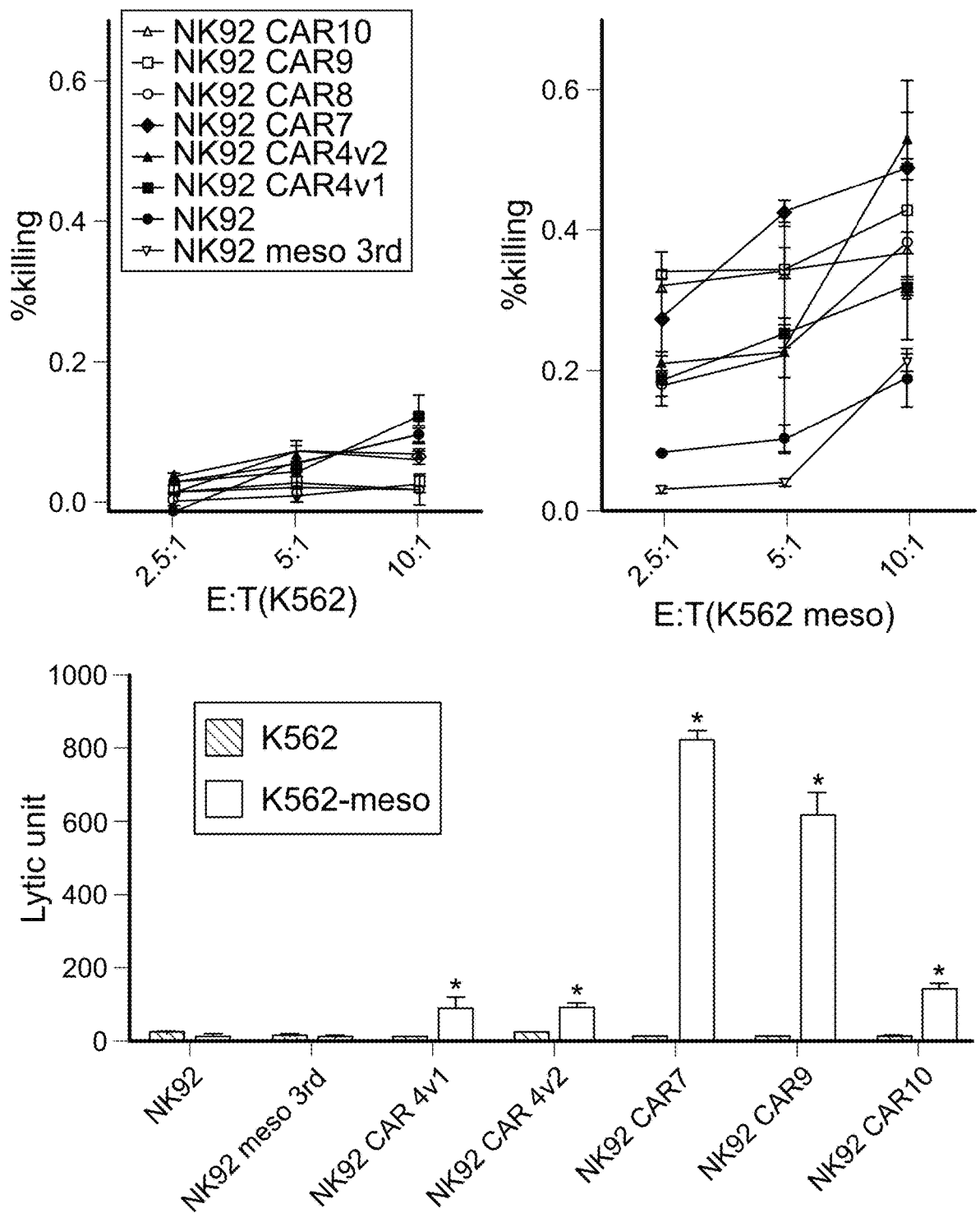
FIG. 10. Data showing cytotoxicity of NK CARs against K562 cells

FIG. 9 shows cytotoxicity of exemplary NK CARs against K562 cells (upper left panel) and K562 cells expressing mesothelin (upper right panel) that is target for the CARs. These results show markedly improved killing in a mesothelin-specific fashion, most notably for CAR7 and CAR9. The lower panel is a summary of the results expressed in lytic units (Bryant et al., 1992, *J Immunol Methods* 146(1):91-103). CAR 7 and CAR 9 exhibit markedly greater cytotoxicity than the $3^{rd}$ generation T cell CAR used in previous studies (NK92 meso $3^{rd}$). Cytotoxicity was measured using a Cr-51 release assay as previously described (Knorr et al., 2013, *Stem Cells Transl Med* 2(4): 274-283; Woll et al., 2009, *Blood* 113(24):3094-6101; Woll et al., 2005, *J Immunol* 175(8):5095-5103). FIG. 10 shows similar results using two ovarian cancer cell lines that are meso-high (A1497) and meso-low (MA148). NK92 cells with different NK cell-based anti-meso CARs kill in a meso-specific fashion. The bottom panel against reflects a summary expressed in lytic units. Moreover, the NK CARs mediate increased expression of CD107a and/or IFN-γ when stimulated with targets as in FIG. 9 and FIG. 10 (data not shown).

Figure 11:
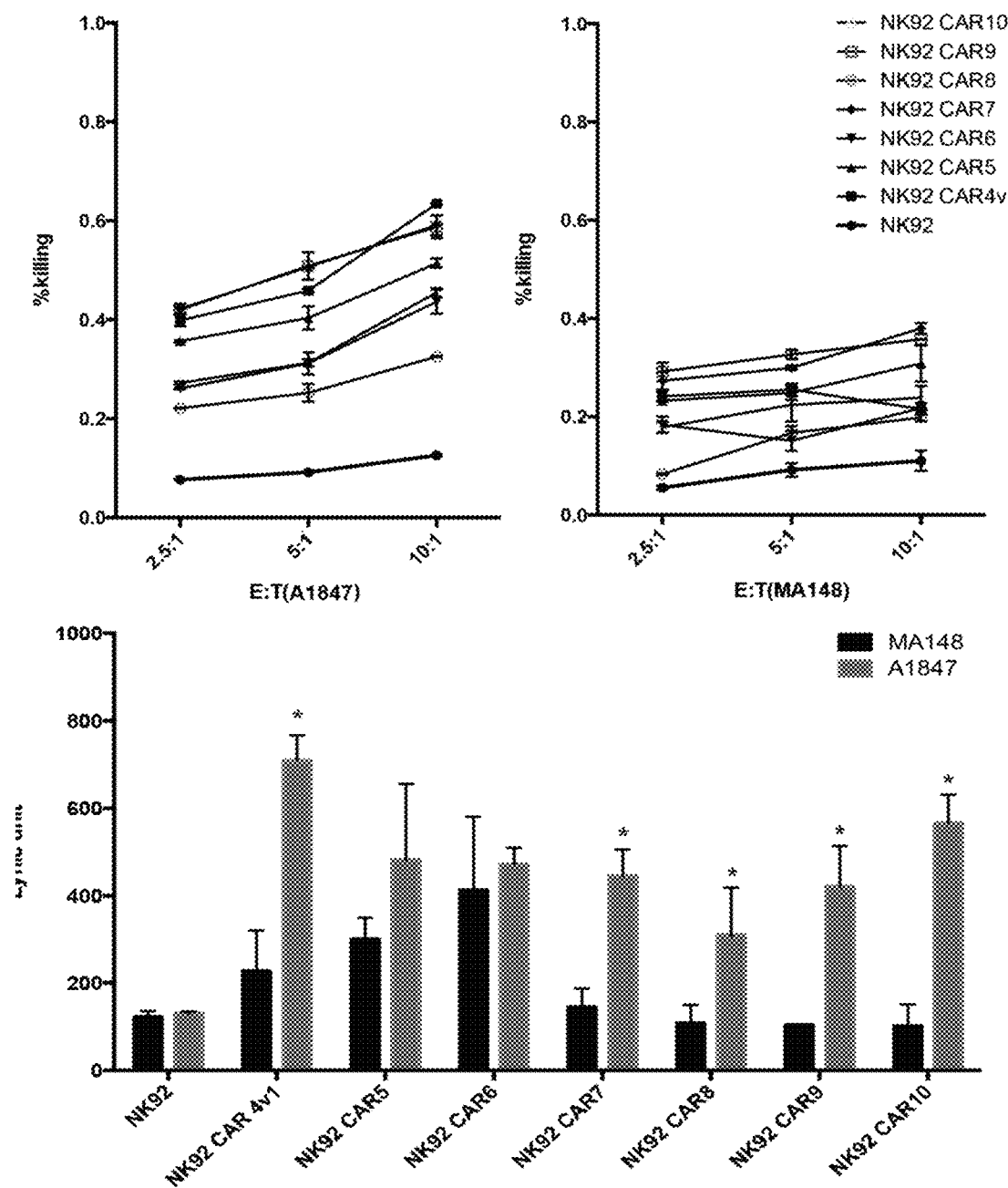
FIG. 11. Data showing cytotoxicity of NK CARs against two ovarian cancer cell lines.
Figure 12:
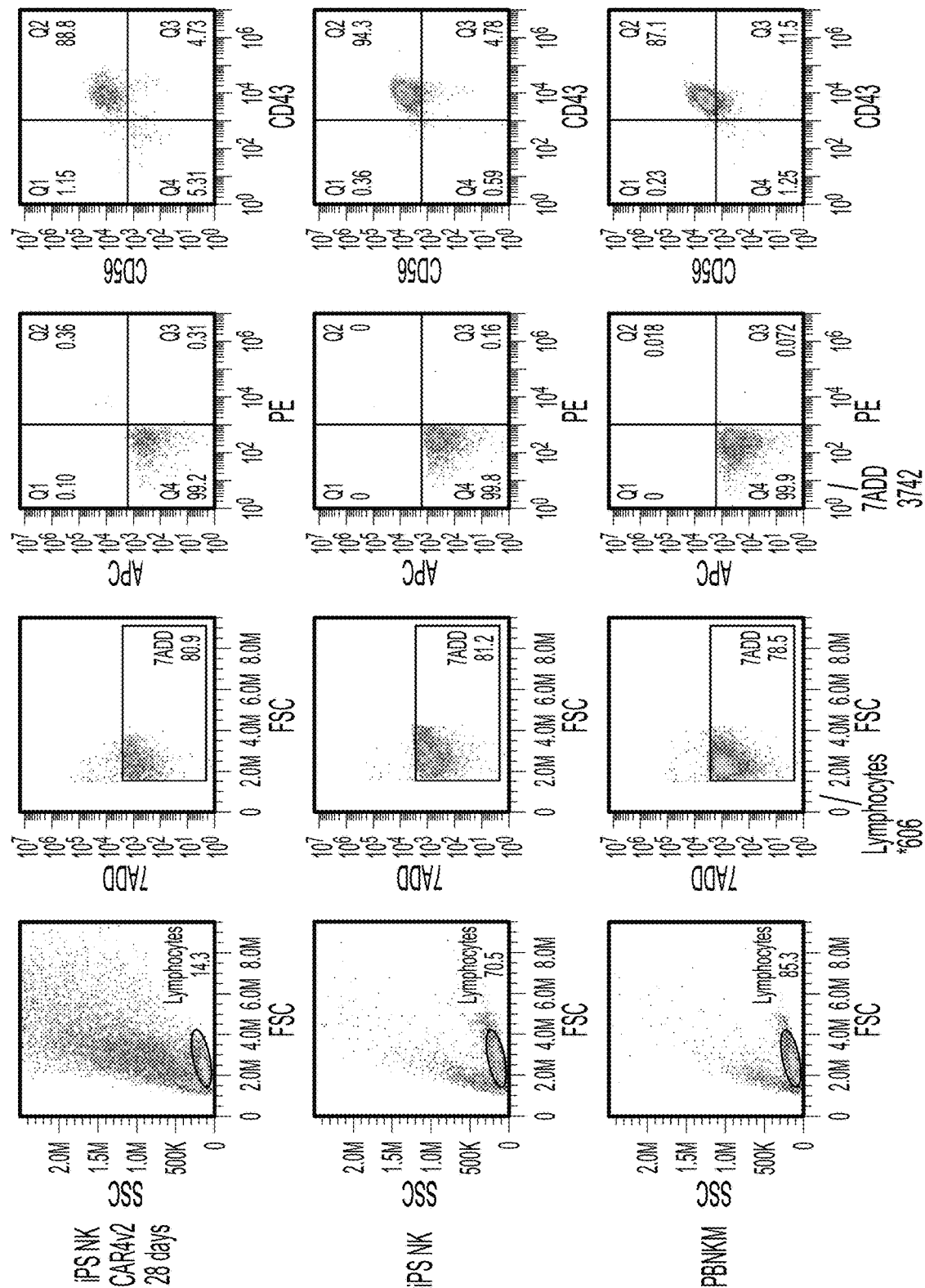
FIG. 12. Data showing expression of an exemplary NK CAR by induced pluripotent stem cells.
Figure 12:
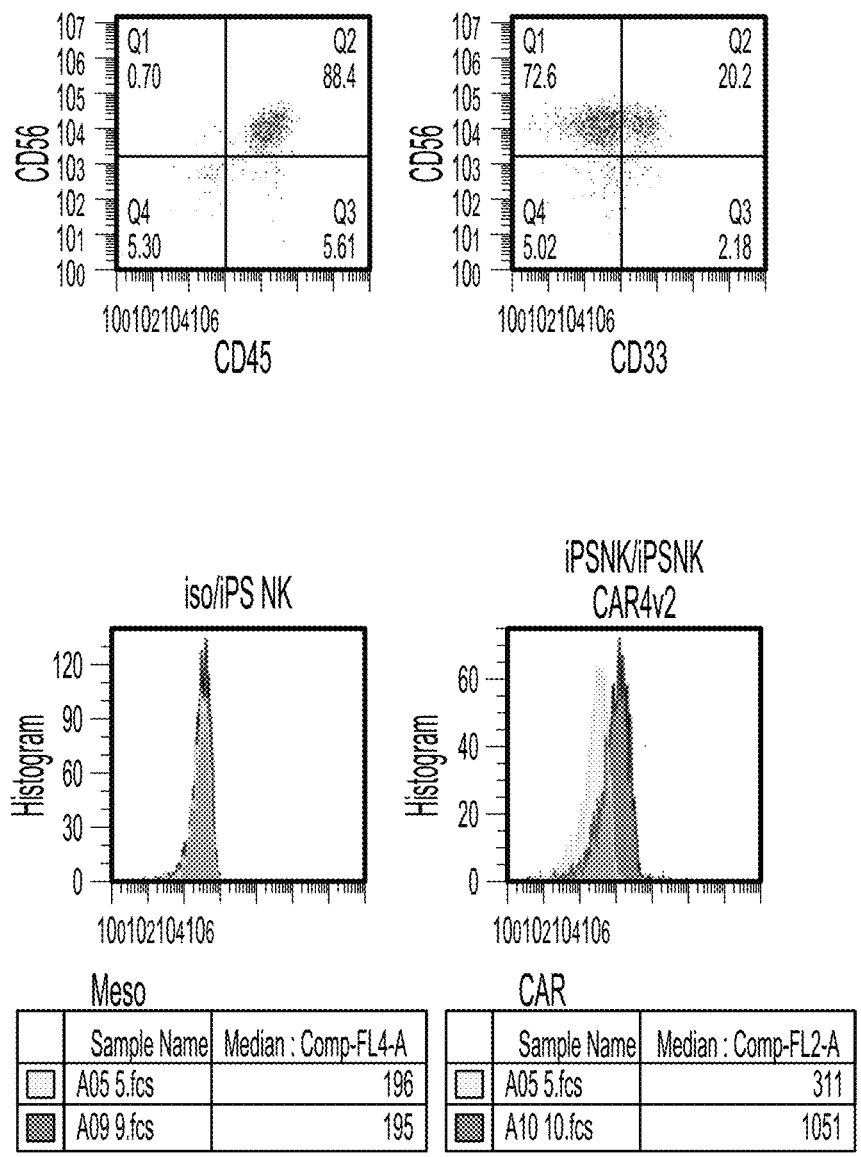
Figure 13:
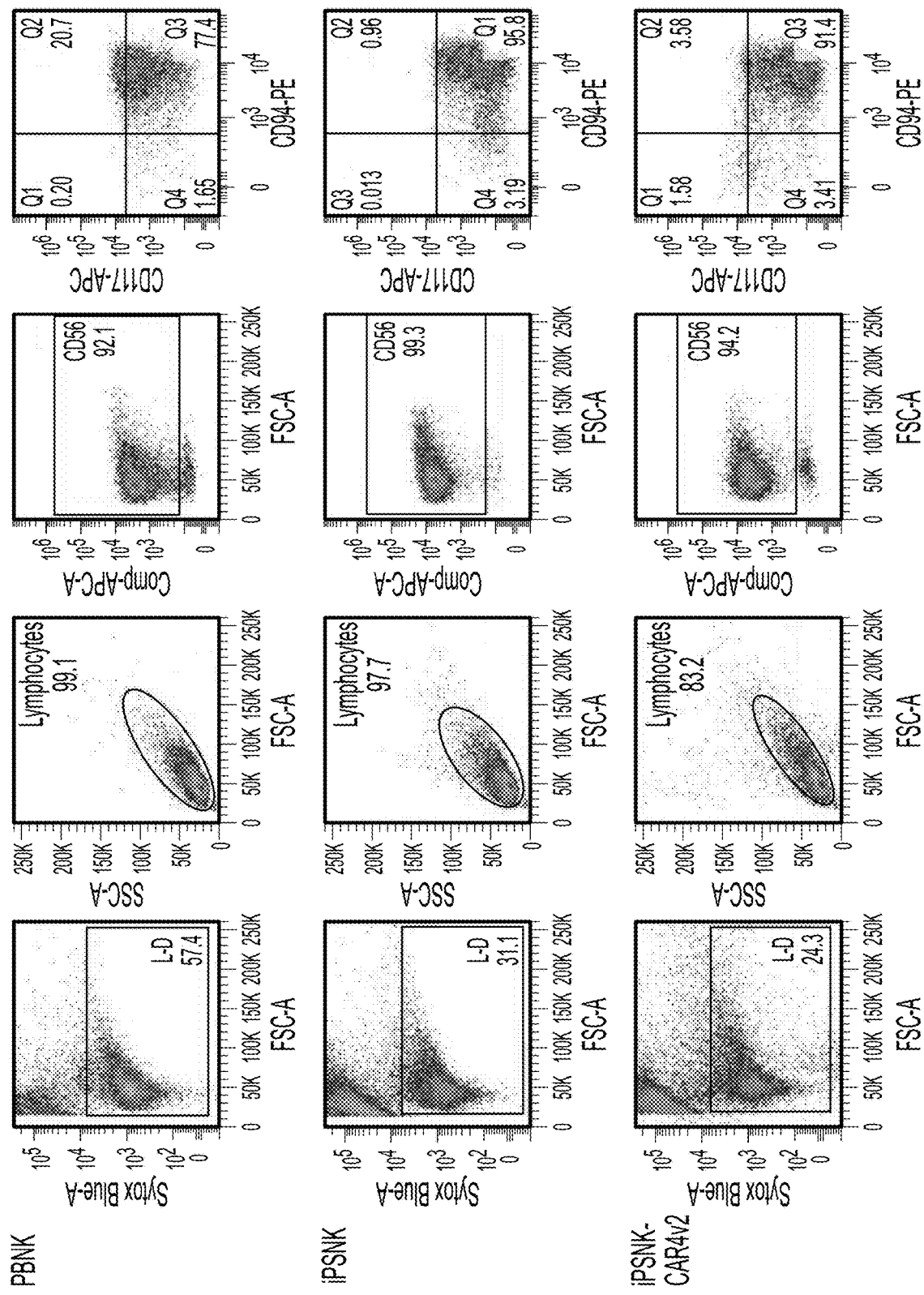
FIG. 13. Data showing surface expression of an exemplary CAR by iPSC-derived NK cells expressing.
Figure 13:
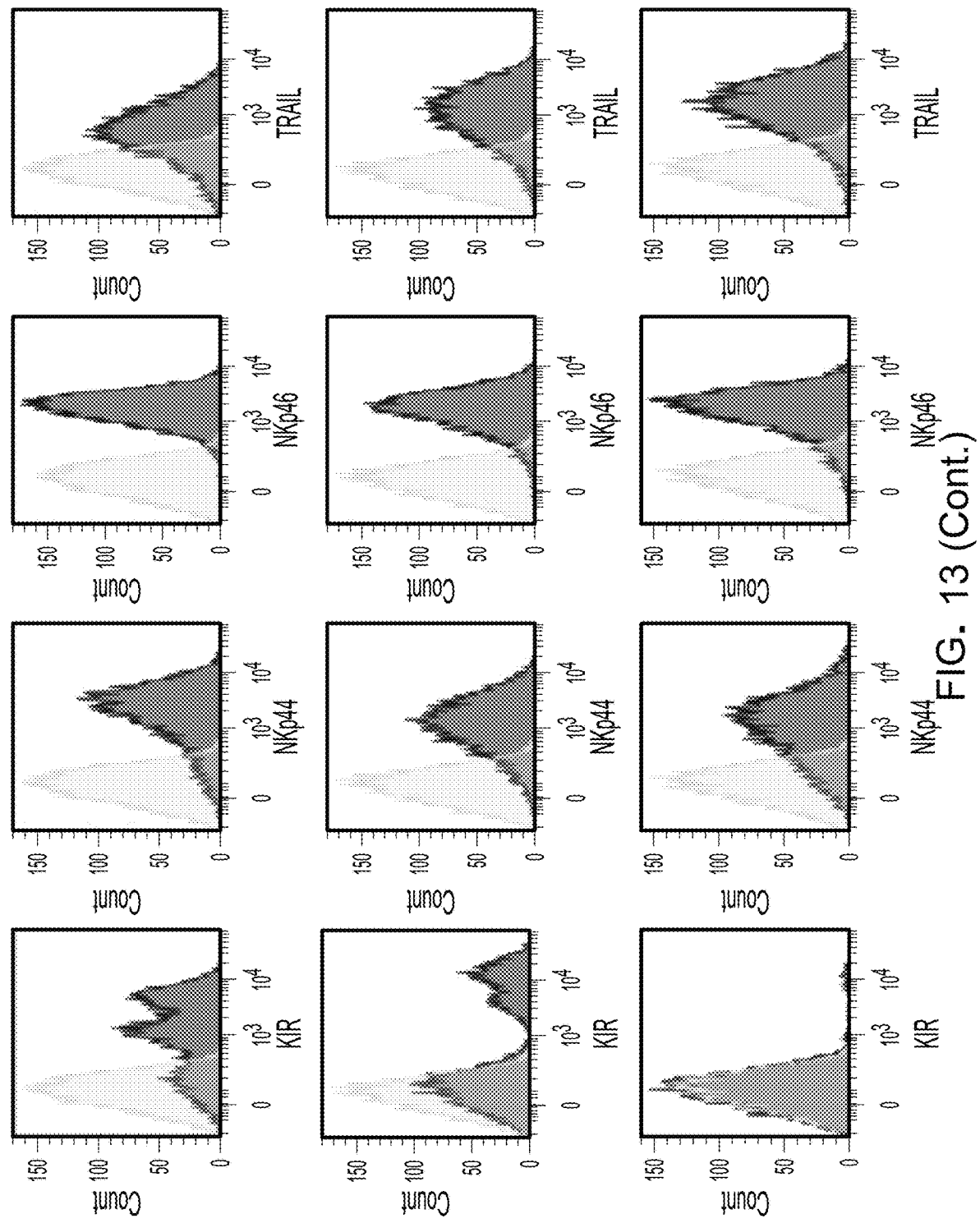
Figure 13:
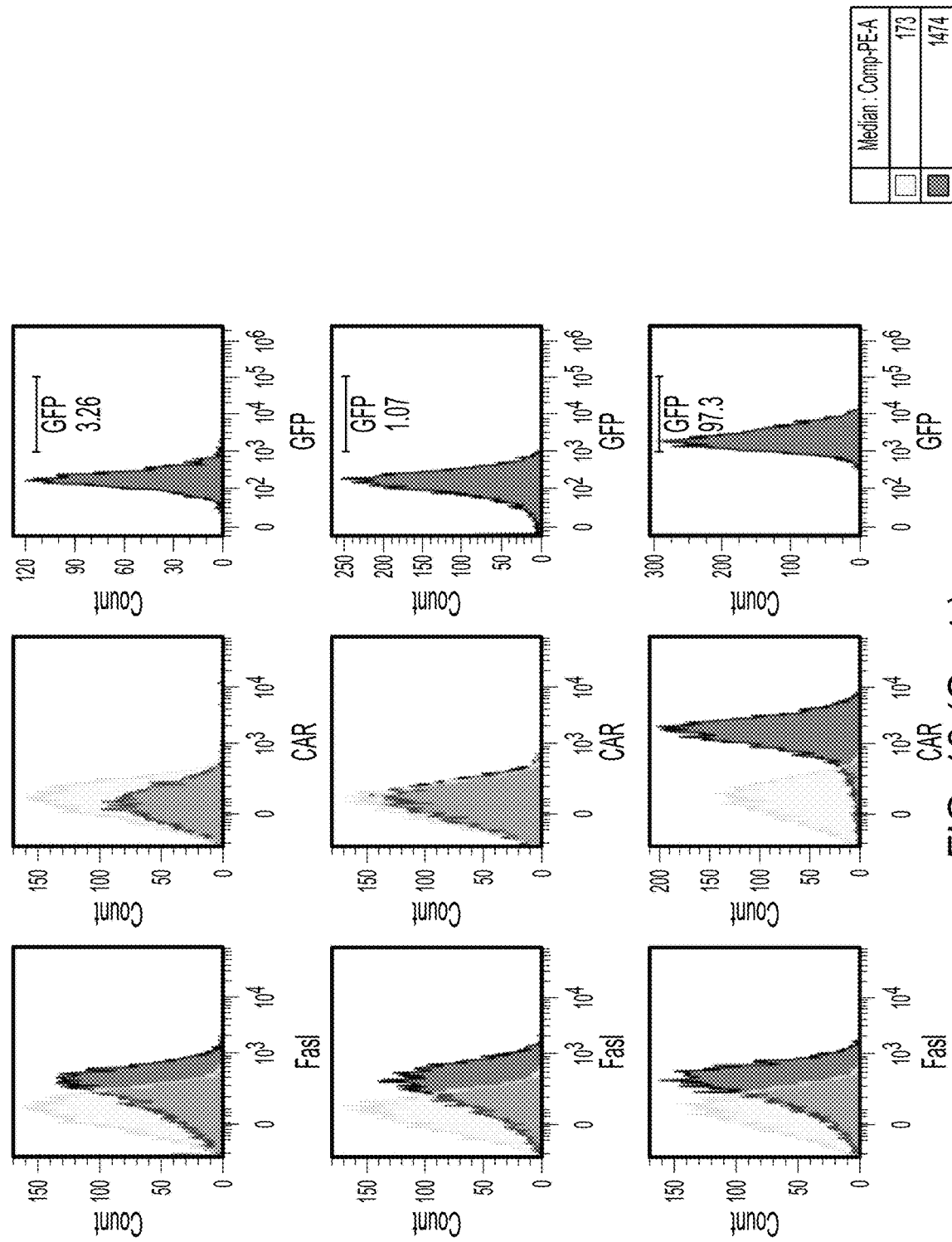

In some embodiments, an NK-specific chimeric antigen receptor as described herein can be expressed in iPSCs, which can then be differentiated into NK cells. The iPSCs may be differentiated as described in Knorr et al., 2013, *Stem Cells Transl Med.* 2(4):274-283 or Ni et al., 2014, *Stem Cells* 32(4):1021-1031. FIG. 11 shows expression of an exemplary NK CAR by induced pluripotent stem cells (iPSCs), as shown by production of CD45+CD56+ cells (top row, $5^{th}$ panel). FIG. 12 shows CAR surface expression by iPSC-derived NK cells. The bottom three rows of FIG. 12 show CAR expression only on the surface of iPSC-CAR4v2 ($4^{th}$ column, bottom three rows) compared to the PB-NK cells and iPSC-NK cells that don't express CARs (unmodified control cells, $4^{th}$ column, row 4 and row 5). Other panels in FIG. 11 and FIG. 12 show other typical NK cell surface antigens/receptors on the iPSC-CAR4v2 are similar to those found on the unmodified control cells. These results indicate that iPSC-derived NK cells can exhibit the same target-specific cytotoxicity as the mesothelin-targeted-CAR-expressing NK cells in FIG. 9 and FIG. 10.

Figure 14:
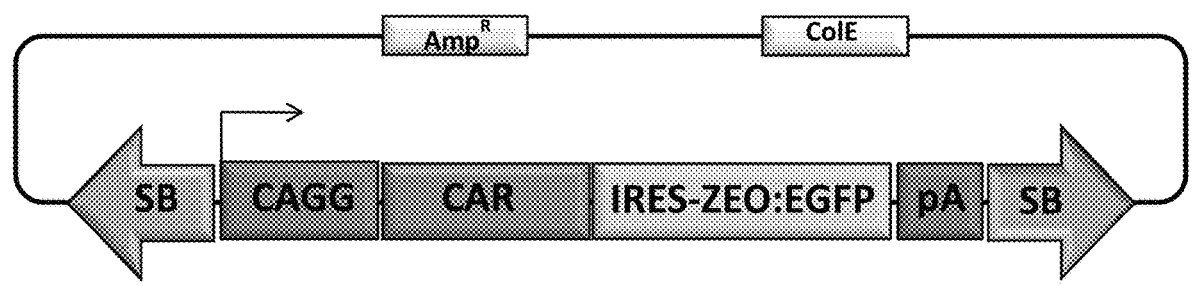
FIG. 14. An exemplary generalized NK CAR vector construct.
Figure 15:
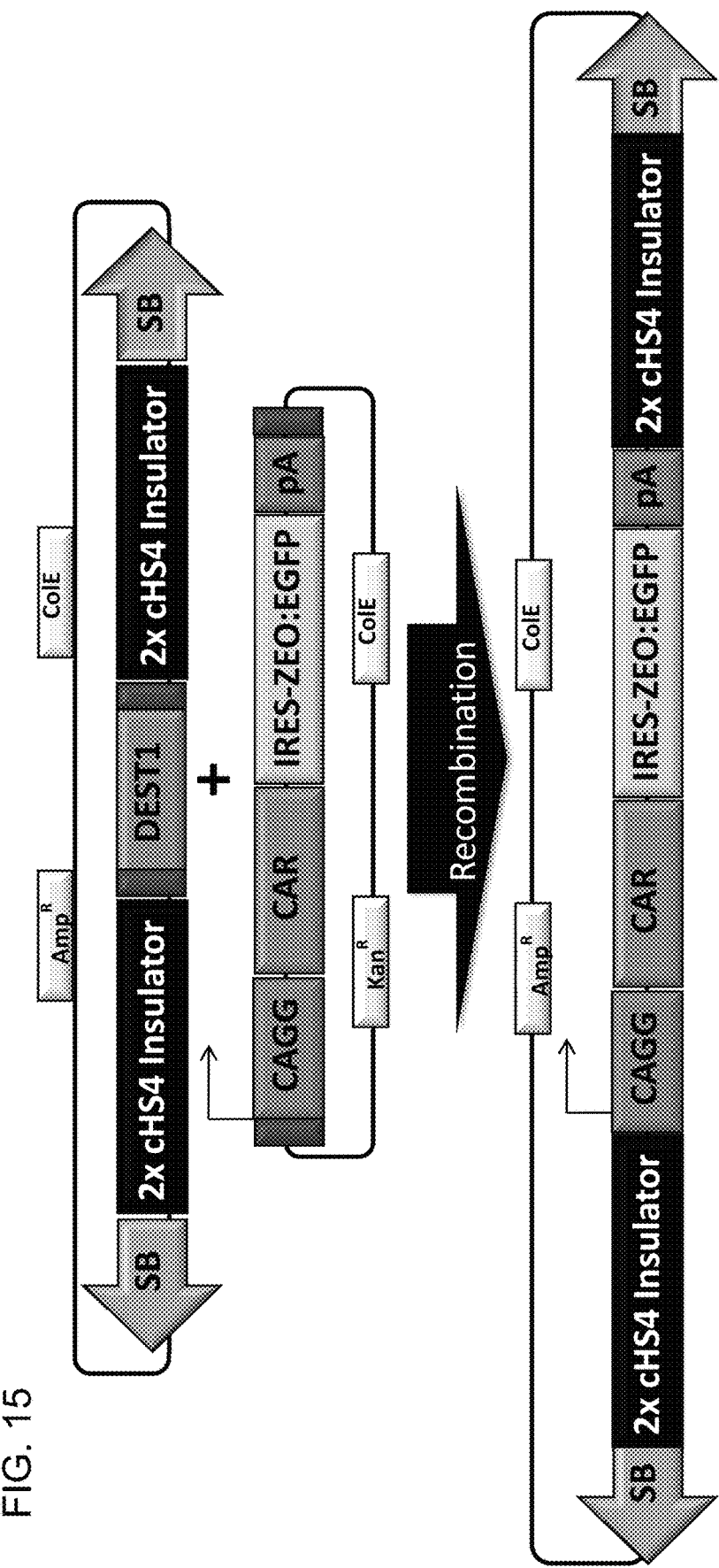
FIG. 15. An exemplary generalized NK CAR vector construct. Tandem cHS4 insulators can inhibit silencing of the CAR vector and, therefore, improve expression of the CAR in NK cells and iPSCs.

A polynucleotide that encodes an NK CAR construct may be introduced into an NK cell or iPSC using conventional transfection method. Thus, while described herein in the context of an exemplary embodiment in which a polynucleotide encoding the CAR is transfected into cells using a Sleeping Beauty transposon system, NK cells (and/or iPSCs) may be modified using any suitable transfection method. FIG. 14 illustrates an exemplary vector construct that may be used to modify NK cells (and/or iPSCs) to express a chimeric antigen receptor. FIG. 15 illustrates the construction of an alternative exemplary vector that further includes tandem cHS4 insulators (Aker et al., 2007, *Hum Gene Ther* 18(4):333-343), which can inhibit silencing of the CAR vector and, therefore, improve expression of the CAR in NK cells and iPSCs.

NK cells and/or iPSCs modified to express a chimeric antigen receptor described herein may be formulated into a pharmaceutical composition along with a "carrier" for delivery to a subject having a condition at least partially characterized by cells that can be targets of NK cytotoxicity. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with NK cells (and/or iPSCs) modified to express a chimeric antigen receptor without causing any undesirable biological effects or interacting in a deleterious manner with any of the other components of the pharmaceutical composition in which it is contained.

The pharmaceutical composition may be formulated in a variety of forms adapted to a preferred route of administration. Thus, a composition can be administered via known routes including, for example, parenteral (e.g., intradermal, transcutaneous, subcutaneous, intramuscular, intravenous, intraperitoneal, etc.) or topical (e.g., intratracheal, intrapulmonary, etc.). A composition also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing NK cells (and/or iPSCs) modified to express a chimeric antigen receptor into association with a carrier that constitutes one or more accessory ingredients. In general, a formulation may be prepared by uniformly and/or intimately bringing the NK cells (and/or iPSCs) into association with, for example, a liquid carrier.

A pharmaceutical composition that includes NK cells (and/or iPSCs) modified to express a chimeric antigen receptor may be provided in any suitable form including but not limited to a solution, a suspension, an emulsion, a spray, an aerosol, or any form of mixture. The composition may be delivered in formulation with any pharmaceutically acceptable excipient, carrier, or vehicle.

The amount of NK cells (and/or iPSCs) modified to express a chimeric antigen receptor that is administered to a subject can vary depending on various factors including, but not limited to, the weight, physical condition, and/or age of the subject, whether one or more chimeric antigen receptors are being administered, and/or the route of administration. Thus, the absolute amount of NK cells (and/or iPSCs) included in a given unit dosage form can vary widely, and depends upon factors such as the species, age, weight and physical condition of the subject, as well as the method of administration. Accordingly, it is not practical to set forth generally the amount that constitutes an amount of NK cells (and/or iPSCs) modified to express a chimeric antigen receptor that is effective for each and/or all possible applications. Those of ordinary skill in the art, however, can readily determine the appropriate amount with due consideration of such factors.

In some embodiments, the method can include administering a sufficient number of NK cells (and/or iPSCs) modified to express a chimeric antigen receptor to provide a dose of, for example, from about $10^5$ cells/kg to about $10^{10}$ cells/kg to the subject, although in some embodiments the methods may be performed by administering an amount of NK cells (and/or iPSCs) in a dose outside this range. In some of these embodiments, the method includes administering sufficient NK cells (and/or iPSCs) modified to express a chimeric antigen receptor to provide a dose of from about $10^7$ cells/kg to about $10^8$ cells/kg to the subject, for example, a dose of from about $1\times10^7$ cells/kg to about $8\times10^7$ cells/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184.

In some embodiments, the pharmaceutical composition that includes NK cells (and/or iPSCs) modified to express a chimeric antigen receptor may be administered, for example, from a single dose to multiple doses per week, although in some embodiments the method can be performed by administering the pharmaceutical composition at a frequency outside this range. In certain embodiments, the pharmaceutical composition may be administered from about once per month to about five times per week.

Generally, the pharmaceutical composition is administered to a subject in an amount, and in a dosing regimen effective to reduce, limit the progression of, ameliorate, or resolve, to any extent, the symptoms or clinical signs of the condition. As used herein, "ameliorate" refers to any reduction in the extent, severity, frequency, and/or likelihood of a symptom or clinical sign characteristic of a particular condition. "Symptom" refers to any subjective evidence of disease or of a patient's condition. "Sign" or "clinical sign" refers to an objective physical finding relating to a particular condition capable of being found by one other than the patient.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the exemplary embodiments described above. It is to be understood that the particular examples, materials, amounts, and procedures are to be interpreted broadly in accordance with the scope and spirit of the invention as set forth herein.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A chimeric antigen receptor molecule comprising, in an N-terminus to C-terminus orientation: an ectodomain comprising an antigen recognition region; a hinge; a transmembrane domain comprising a transmembrane region of NKG2D (cluster of differentiation 314 or CD314) in reverse orientation as compared to native NKG2D that natively has an extracellular C-terminus; and an endodomain comprising a functional signaling domain that activates a Natural Killer (NK) cell, wherein said functional signaling domain is selected from the group consisting of:
- (a) a 2B4 (cluster of differentiation 244 or CD244) intracellular domain (ICD) and a CD3 zeta (CD3ζ) signaling domain;
- (b) a 41BB (cluster of differentiation 137 or CD137) ICD and a CD3ζ signaling domain;
- (c) a DAP12 (DNAX activation protein of 12 kDa) ICD and a CD3ζ signaling domain;
- (d) a 2B4 ICD, a 41BB ICD and a CD3ζ signaling domain;
- (e) a IL21R ICD and a CD3ζ signaling domain; and
- (f) a 41BB ICD, a 2B4 ICD and a CD3ζ signaling domain.

2. The chimeric antigen receptor of claim 1 wherein the antigen recognition domain specifically binds an antigen associated with a disease.

3. The chimeric antigen receptor of claim 1 wherein the antigen recognition domain specifically binds a tumor antigen.

4. The chimeric antigen receptor of claim 1 wherein the ectodomain further comprises a signal peptide or leader sequence.

5. The chimeric antigen receptor of claim 1, wherein said hinge is a CD8α hinge.

6. A pharmaceutical composition comprising an NK cell that expresses the chimeric antigen receptor of claim 5.

7. The pharmaceutical composition of claim 6, wherein the NK cell is derived from an iPSC.

\* \* \* \* \*

UNITED STATES PATENT AND TRADEMARK OFFICE
CERTIFICATE OF CORRECTION

PATENT NO. : 10,640,570 B2  Page 1 of 1
APPLICATION NO. : 15/546177
DATED : May 5, 2020
INVENTOR(S) : Dan Samuel Kaufman, David Lee Lampi Hermanson and Branden Scott Moriarity It is certified that error appears in the above-identified patent and that said Letters Patent is hereby corrected as shown below:

On the Title Page

Column 2, Other Publications, first publication, Line 2, replace "specWc" with -- specific --; and In the Claims Column 9, Line 27, replace "claim 5." with -- claim 1. --.

Signed and Sealed this
Fourth Day of August, 2020

Andrei Iancu
*Director of the United States Patent and Trademark Office*